(12) United States Patent
Sacolick et al.

(10) Patent No.: US 8,198,891 B2
(45) Date of Patent: Jun. 12, 2012

(54) SYSTEM, METHOD, AND APPARATUS FOR MAGNETIC RESONANCE RF-FIELD MEASUREMENT

(75) Inventors: Laura I. Sacolick, Munich (DE); Mika W. Vogel, Landshut (DE); Florian Wiesinger, Freising (DE); Ileana Hancu, Clifton Park, NY (US)

(73) Assignee: General Electric Company, Niskayuna, NY (US)

( * ) Notice: Subject to any disclaimer, the term of this patent is extended or adjusted under 35 U.S.C. 154(b) by 296 days.

(21) Appl. No.: 12/484,457

(22) Filed: Jun. 15, 2009

(65) Prior Publication Data

US 2010/0315084 A1 Dec. 16, 2010

(51) Int. Cl.
*G01V 3/00* (2006.01)
(52) U.S. Cl. ...................................................... 324/307
(58) Field of Classification Search ........... 324/300–322
See application file for complete search history.

(56) References Cited

U.S. PATENT DOCUMENTS

| | | | |
|---|---|---|---|
| 6,268,728 B1 | 7/2001 | Morrell | |
| 7,053,618 B2 | 5/2006 | Zhu | |
| 7,075,301 B2 | 7/2006 | Zhu | |
| 7,233,143 B2 * | 6/2007 | Moriguchi et al. | 324/307 |
| 7,233,818 B1 * | 6/2007 | Aletras et al. | 600/410 |
| 7,706,857 B2 * | 4/2010 | Aletras et al. | 600/410 |
| 2007/0108976 A1 | 5/2007 | Morich et al. | |
| 2008/0100292 A1 | 5/2008 | Hancu | |
| 2008/0150528 A1 | 6/2008 | Cunningham et al. | |

OTHER PUBLICATIONS

Vierkotter, "Applications of the Bloch—Siegert Shift in Solid-State Proton-Dipolar-Decoupled 19F MAS NMR," Journal of Magnetic Resonance, Series A 118, 1996, pp. 84-93, Article No. 0012.
Cernicanu et al., "Absolute B1-Mapping from Repeated Varying Flip Angle RF Excitations," Proc. Intl. Soc. Mag. Reson. Med., vol. 14, 2006, p. 3369.
Morrell, "A Phase-Sensitive Method of Flip Angle Mapping," Magnetic Resonance in Medicine, vol. 60, 2008, pp. 889-894.
Park et al., "B1 Mapping Using Phase Information Created by Frequency-Modulated Pulses," Proc. Intl. Soc. Mag. Reson. Med., vol. 16, 2008, p. 361.
Treier et al., "Optimized and Combined T1 and B1 Mapping Technique for Fast and Accurate T1 Quantification in Contrast-Enhanced Abdominal MRI," Magnetic Resonance in Medicine, vol. 57, 2007, pp. 568-576.

* cited by examiner

*Primary Examiner* — Dixomara Vargas
(74) *Attorney, Agent, or Firm* — Scott J. Asmus

(57) ABSTRACT

An apparatus, system, and method including a magnetic resonance imaging (MRI) apparatus includes a magnetic resonance imaging (MRI) system having a plurality of gradient coils positioned about a bore of a magnet, and an RF transceiver system and an RF switch controlled by a pulse module to transmit RF signals to an RF coil assembly to acquire MR images, and a computer. The computer is programmed to apply a first off-resonant radio frequency (RF) pulse at a first frequency different than the resonant frequency to a plurality of nuclei excited at a resonant frequency, acquire a first signal from the plurality of nuclei after application of the first off-resonant RF pulse, determine a phase shift from the first signal based on the first off-resonant RF pulse, determine a B1 field based on the phase shift, and store the B1 field on a computer readable storage medium.

20 Claims, 5 Drawing Sheets

154 — IMPLEMENT A FIRST SCAN UTILIZING AN OFF-RESONANCE RF PULSE

156 — IMPLEMENT A SECOND SCAN UTILIZING AN OFF-RESONANCE RF PULSE

158 — IMPLEMENT A THIRD SCAN WITHOUT AN OFF-RESONANCE RF PULSE

160 — DETERMINE B1 FIELD BASED ON THE FIRST AND SECOND SCANS

162 — DETERMINE B0 FIELD BASED ON THE FIRST, SECOND, AND THIRD SCANS

SYSTEM, METHOD, AND APPARATUS FOR MAGNETIC RESONANCE RF-FIELD MEASUREMENT

GOVERNMENT RIGHTS IN THE INVENTION

This invention was made with government support under contract number 5R01EB005307-02 awarded by the National Institute of Health. The government has certain rights in the invention.

BACKGROUND OF THE INVENTION

The present invention relates generally to medical imaging systems and, more particularly, to determination of $B_1$ fields associated with magnetic resonance imaging.

When a substance such as human tissue is subjected to a uniform magnetic field (polarizing field $B_0$), the individual magnetic moments of the spins in the tissue attempt to align with this polarizing field, but precess about it in random order at their characteristic Larmor frequency. If the substance, or tissue, is subjected to a magnetic field (excitation field $B_1$) which is in the x-y plane and which is near the Larmor frequency, the net aligned moment, or "longitudinal magnetization", $M_z$, may be rotated, or "tipped", into the x-y plane to produce a net transverse magnetic moment $M_t$. A signal is emitted by the excited spins after the excitation signal $B_1$ is terminated and this signal may be received and processed to form an image.

When utilizing these signals to produce images, magnetic field gradients ($G_x$, $G_y$, and $G_z$) are employed. Typically, the region to be imaged is scanned by a sequence of measurement cycles in which these gradients vary according to the particular localization method being used. The resulting set of received nuclear magnetic resonance (NMR) signals are digitized and processed to reconstruct the image using one of many well known reconstruction techniques.

There are a variety of techniques used to determine if the $B_1$ field produced by a magnetic resonance coil or array is homogeneous or to what degree the field is inhomogeneous. Such techniques are often referred to as $B_1$ mapping. In general, $B_1$ mapping techniques may either implement spatially or non-spatially resolved $B_1$ measurements. $B_1$ measurements are spatially resolved if one or more spatial encoding gradients are applied during acquisition and, in contrast, $B_1$ measurements are non-spatially resolved when spatial encoding gradients are not utilized during $B_1$ measurements. Among other things, $B_1$ maps can be used to adjust transmit gain to produce a radio frequency (RF) pulse at a specific flip angle, to design multi-transmit channel RF pulses, and to aide in the implementation of chemical shift imaging. $B_1$ mapping can also serve as an aide in T1 mapping and/or other quantitative MR imaging techniques. Some $B_1$ mapping techniques are T1 dependent. That is, the signal utilized for $B_1$ is often weighted as a function of T1 relaxation. Other $B_1$ mapping techniques are $B_0$ or chemical shift dependent. Still other techniques are inaccurate over certain ranges of $B_1$ field, and/or are dependent on large RF power depositions.

Of the $B_1$ mapping techniques, a sub-class of such techniques contains techniques that may be referred to as phase-based $B_1$ mapping techniques. One such phase-based $B_1$ mapping technique uses the phase accrued from a $2\alpha$-$\alpha$ flip angle sequence to determine $B_1$. Although such a technique is more accurate than others over a larger range of flip angles, such a technique is $B_0$ dependent and often relies on a relatively long repetition time (TR) requirement.

Another phase-based $B_1$ mapping technique utilizes a $B_1$-dependent phase produced by adiabatic hyperbolic secant half- and full-passage pulses. However, the specific absorption rate (SAR) associated with such techniques can limit the clinical application of such techniques at a high magnetic field.

It would therefore be desirable to have a system and apparatus that efficiently determines a $B_1$ or RF field of a magnetic resonance system without some or all the aforementioned drawbacks.

BRIEF DESCRIPTION OF THE INVENTION

Embodiments of the invention provide a system, apparatus, and method for determining $B_1$ fields that overcome some or all the aforementioned drawbacks.

In accordance with one aspect of the invention, a magnetic resonance imaging (MRI) apparatus includes a magnetic resonance imaging (MRI) system having a plurality of gradient coils positioned about a bore of a magnet, and an RF transceiver system and an RF switch controlled by a pulse module to transmit RF signals to an RF coil assembly to acquire MR images, and a computer. The computer is programmed to apply a first off-resonant radio frequency (RF) pulse at a first frequency different than the resonant frequency to a plurality of nuclei excited at a resonant frequency, acquire a first signal from the plurality of nuclei after application of the first off-resonant RF pulse, determine a phase shift from the first signal based on the first off-resonant RF pulse, determine a B1 field based on the phase shift, and store the B1 field on a computer readable storage medium.

In accordance with another aspect of the invention, a computer readable storage medium includes a computer program stored thereon. The computer program includes instructions which when executed by a computer cause the computer to cause a pulse generator to apply a first off-resonant radio frequency (RF) pulse to a plurality of excited nuclei, receive a first signal from the plurality of excited nuclei via at least one magnetic resonant (MR) receive coil after application of the first off-resonant RF pulse, determine a phase shift induced by the first off-resonant RF pulse, determine a B1 field based on the phase shift, and store the B1 field on a storage device coupled to an MR imaging apparatus. The first off-resonant RF pulse is configured to shift a resonant frequency of the plurality of nuclei.

In accordance with yet another aspect of the invention, a method of determining a magnetic field includes shifting a resonating frequency of a plurality of nuclei after the plurality of nuclei are excited at a first resonating frequency, acquiring a first signal with a magnetic resonance (MR) receive coil from the plurality of nuclei after shifting the resonating frequency, determining a phase shift based on the first signal, and storing the phase shift on a computer readable storage medium coupled to an MR apparatus.

Various other features and advantages will be made apparent from the following detailed description and the drawings.

BRIEF DESCRIPTION OF THE DRAWINGS

The drawings illustrate preferred embodiments presently contemplated for carrying out the invention.

In the drawings:

FIG. 5 is a flowchart depicting a technique for determining a $B_1$ field and a $B_0$ field according to an embodiment of the invention.

DETAILED DESCRIPTION

Figure 1:
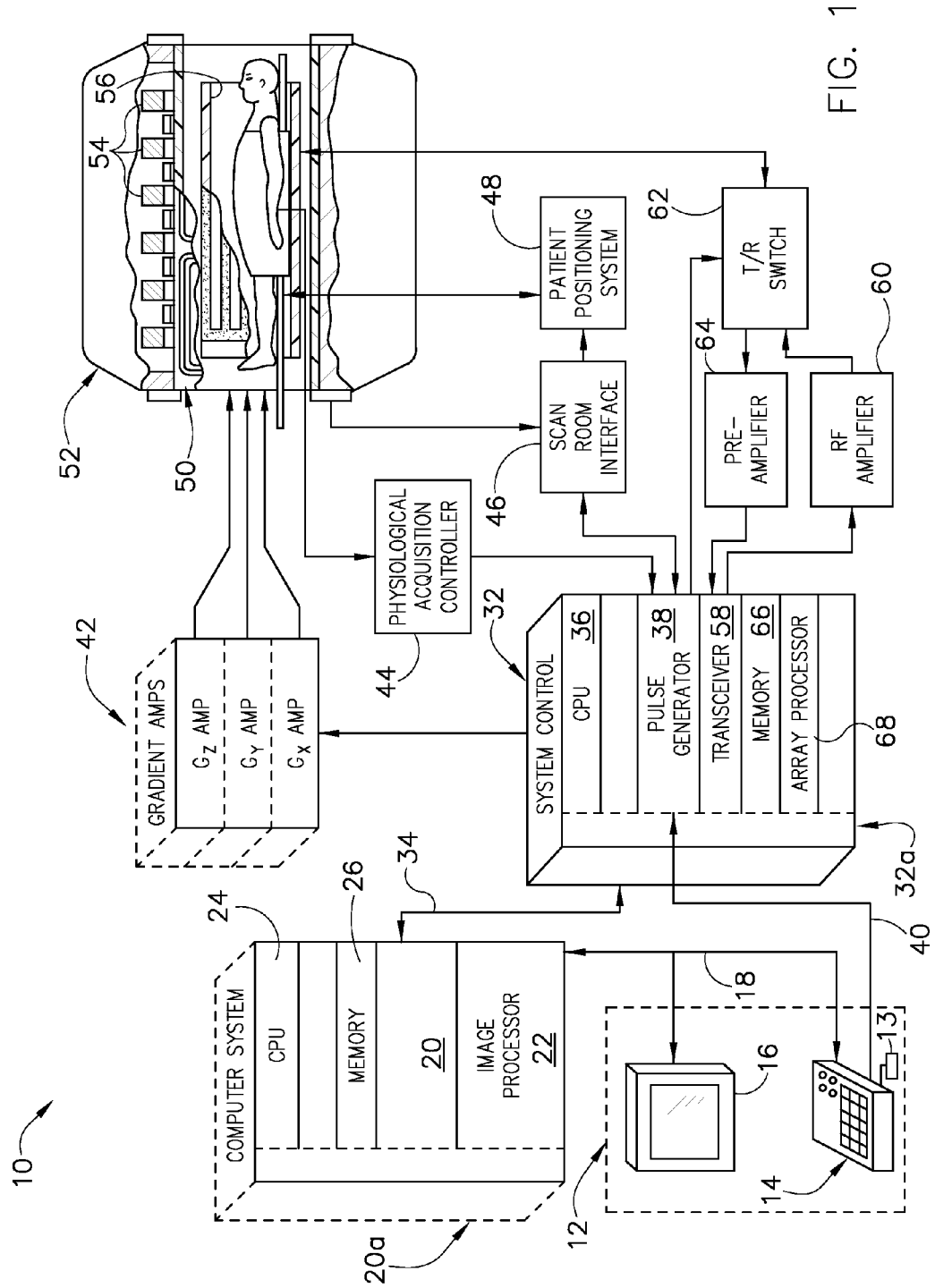
FIG. 1 is a schematic diagram of an exemplary MR imaging system for use with embodiments of the present invention.

Referring to FIG. 1, the major components of an exemplary magnetic resonance imaging (MRI) system 10 incorporating embodiments of the present invention are shown. The operation of the system is controlled from an operator console 12 which includes a keyboard or other input device 13, a control panel 14, and a display screen 16. The console 12 communicates through a link 18 with a separate computer system 20 that enables an operator to control the production and display of images on the display screen 16. The computer system 20 includes a number of modules which communicate with each other through a backplane 20a. These include an image processor module 22, a CPU module 24 and a memory module 26 that may include a frame buffer for storing image data arrays. The computer system 20 is linked to archival media devices, permanent or back-up memory storage or a network for storage of image data and programs, and communicates with a separate system control 32 through a high speed serial link 34. The input device 13 can include a mouse, joystick, keyboard, track ball, touch activated screen, light wand, voice control, or any similar or equivalent input device, and may be used for interactive geometry prescription.

The system control 32 includes a set of modules connected together by a backplane 32a. These include a CPU module 36 and one or more pulse generator modules 38 which connect to the operator console 12 through a serial link 40. It is through link 40 that the system control 32 receives commands from the operator to indicate the scan sequence that is to be performed. The pulse generator module 38 operates the system components to carry out the desired scan sequence and produces data which indicates the timing, strength and shape of the RF pulses produced, and the timing and length of the data acquisition window. The pulse generator module 38 connects to a set of gradient amplifiers 42, to indicate the timing and shape of the gradient pulses that are produced during the scan. The pulse generator module 38 can also receive patient data from a physiological acquisition controller 44 that receives signals from a number of different sensors connected to the patient, such as ECG signals from electrodes attached to the patient. And finally, the pulse generator module 38 connects to a scan room interface circuit 46 which receives signals from various sensors associated with the condition of the patient and the magnet system. It is also through the scan room interface circuit 46 that a patient positioning system 48 receives commands to move the patient to the desired position for the scan.

The gradient waveforms produced by the pulse generator module 38 are applied to the gradient amplifier system 42 having Gx, Gy, and Gz amplifiers. Each gradient amplifier excites a corresponding physical gradient coil in a gradient coil assembly generally designated 50 to produce the magnetic field gradients used for spatially encoding acquired signals. The gradient coil assembly 50 forms part of a magnet assembly 52 which includes a polarizing magnet 54 and a whole-body RF coil 56. In an embodiment of the invention, RF coil 56 is a multi-channel coil. A transceiver module 58 in the system control 32 produces pulses which are amplified by one or more RF amplifiers 60 and coupled to the RF coil 56 by a transmit/receive switch 62. The resulting signals emitted by the excited nuclei in the patient may be sensed by the same RF coil 56 and coupled through the transmit/receive switch 62 to a preamplifier 64. The amplified MR signals are demodulated, filtered, and digitized in the receiver section of the transceiver 58. The transmit/receive switch 62 is controlled by a signal from the pulse generator module 38 to electrically connect the RF amplifier 60 to the coil 56 during the transmit mode and to connect the preamplifier 64 to the coil 56 during the receive mode. It is recognized that RF coil 56 or an array may take the form of a dedicated receive coil integrated into a patient table. Alternatively, it is also recognized that a separate RF coil (for example, a surface coil) or array may be enabled by transmit/receive switch 62 and may be used in addition to or in lieu of RF coil 56.

The MR signals picked up by the multi-channel RF coil 56 are digitized by the transceiver module 58 and transferred to a memory module 66 in the system control 32. A scan is complete when an array of raw k-space data has been acquired in the memory module 66. This raw k-space data is rearranged into separate k-space data arrays for each image to be reconstructed, and each of these is input to an array processor 68 which operates to Fourier transform the data into an array of image data. This image data is conveyed through the serial link 34 to the computer system 20 where it is stored in memory. In response to commands received from the operator console 12, this image data may be archived in long term storage or it may be further processed by the image processor 22 and conveyed to the operator console 12 and presented on the display 16.

Figure 2:
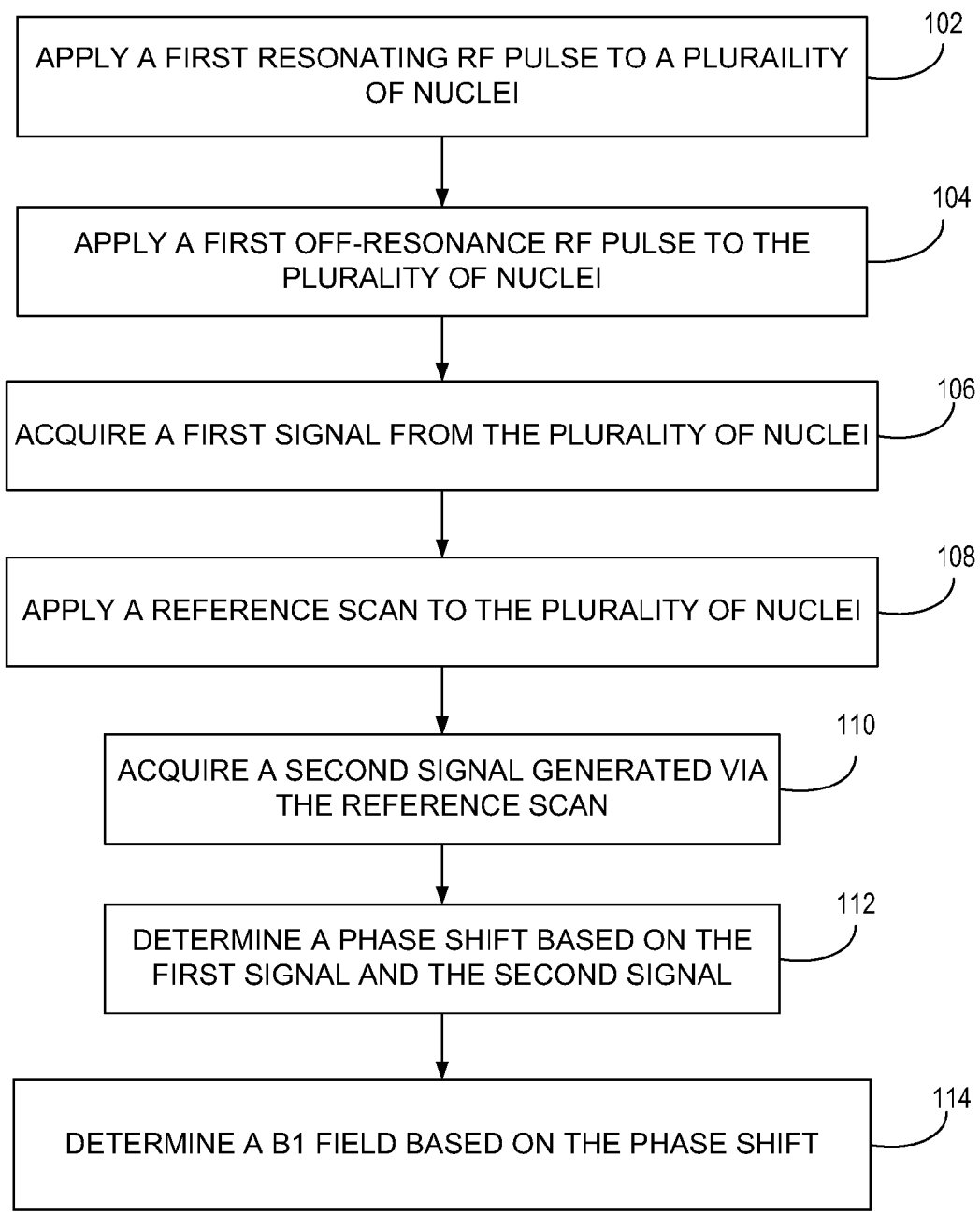
FIG. 2 is a flowchart depicting a technique for determining a $B_1$ field according to an embodiment of the invention.

Referring to FIG. 2, a flowchart depicting a technique 100 for determining a $B_1$ field of a magnetic resonance coil or array according to an embodiment of the invention is shown. Technique 100 begins at block 102, where a first resonating RF pulse is applied to a plurality of nuclei. A resonating RF pulse is an RF pulse tuned to a resonant frequency of a plurality of nuclei subjected to a magnetic field. As such, the application of a resonating RF pulse places the nuclei in an excited state. The parameters of the resonating RF pulse may be arbitrarily chosen by the user. After application of the first resonating RF pulse, a first off-resonance RF pulse is applied to the plurality of excited nuclei at block 104. An off-resonance RF pulse is an RF pulse tuned such that that application of the off-resonance RF pulse to a plurality of nuclei does not place the plurality of nuclei in an excited state. For example, an off-resonance RF pulse is an RF pulse having a particular shape or frequency such that the application thereof to a plurality of nuclei subjected to a magnetic field will not be excited, or will be excited to a minimal extent.

The application of this first off-resonance RF pulse occurs while the plurality of nuclei are already in an excited state. The application of the first off-resonance RF pulse causes the resonance frequency of the plurality of excited nuclei to shift. Such a shift is often referred to as a Bloch-Siegert shift. The magnitude of such a shift is dependent on the $B_1$ field applied to the plurality of excited nuclei.

After application of the first off-resonance RF pulse, a first signal is acquired from the plurality of shifted nuclei at block 106. Proceeding to block 108, a reference scan is applied to again excite the plurality of nuclei. The reference scan includes at least one resonating RF pulse. However, in this embodiment, the reference scan does not include an off-resonance RF pulse. A signal generated via the reference scan is acquired at block 110. That is, a second or additional signal is acquired at block 110. As depicted in the flowchart of FIG. 2, the reference scan and the acquisition of the second signal occur after acquisition of the first signal. However, it is contemplated that in an alternate embodiment, the reference scan and the acquisition of the additional signal may occur prior to the application of the first resonating RF pulse at block 102.

Proceeding to block 112, a phase shift is determined based on the first and second acquired signals. The phase associated with the first signal is the sum of transmit phase, $\phi_{Tx}$, the receive phase, $\phi_{Rx}$, the $B_0$ phase, $\phi_{B0}$, additional sequence-related phase $\phi_{Seq}$ and the Bloch-Siegert phase, $\phi_{BS}$. The Bloch-Siegert phase may be represented in the following manner:

$$\varphi_{BS} = \int_0^T \frac{\gamma B_1^2(t)}{2(\Delta\omega_{RF}(t) + \Delta\omega_{B0})}, \quad \text{(Eqn. 1)},$$

where $B_1$ represents the magnetic field associated with the RF coil or array, $\Delta\omega_{B0}$ represents frequency associated with $B_0$ inhomogeneity and/or chemical shift, and $\Delta\omega_{RF}$ represents the difference between the frequency of the off-resonance RF pulse and the frequency of the resonating RF pulse, where the resonating RF pulse is considered to be at the resonance frequency of the spin system.

As such, the phase, $\phi_1$, associated with the first signal can be represented in the following manner:

$$\phi_1 = (\phi_{Tx} + \phi_{Rx} + \phi_{B0} + \phi_{Seq}) + \phi_{BS} \quad \text{(Eqn. 2)}.$$

The phase of the second signal, since an off-resonance pulse was not played out prior to the acquisition thereof, is not dependant on $\phi_{BS}$. That is, the phase of the second signal is the sum of transmit phase, $\phi_{Tx}$, the receive phase, $\phi_{Rx}$, and $B_0$ phase, $\phi_{B0}$. Accordingly, the phase, $\phi_2$, associated with the second signal can be represented in the following manner:

$$\phi_2 = (\phi_{Tx} + \phi_{Rx} + \phi_{B0} + \phi_{Seq}) \quad \text{(Eqn. 3)}.$$

In one embodiment, the phase difference between the first and second signal determines the phase shift. That is:

$$\phi_1 - \phi_2 = \phi_{BS} \quad \text{(Eqn. 4)}.$$

After determining the phase shift, process control proceeds to block 114, and a $B_1$ field is determined based on the phase shift. According to one embodiment, the following relationship is used to determine the $B_1$ field:

$$B_{1,peak} = \sqrt{\frac{\varphi_{BS}}{\int_0^T \frac{\gamma B_{1,normalized}^2(t)}{2(\Delta\omega_{RF}(t) + \Delta\omega_{B0})} dt}}, \quad \text{(Eqn. 5)},$$

where $B_{1,normalized}$ is the off-resonance pulse shape, normalized so that the highest point of the pulse shape=1. $B_{1,normalized}$ can be considered to equal or substantially equal $B_1(t)/B_{1,peak}$. $B_1(t)$ represents the of the off-resonance pulse as a function of time and $B_{1,peak}$ represents the maximum of $B_1(t)$ (i.e., the magnitude of the off-resonance RF field at the highest point of the RF pulse, and $\omega_{RF}(t)$ represents the offset frequency of the RF pulse as a function of time. That is, $\omega_{RF}(t)$ represents the difference between the resonating RF pulse and the off-resonance RF pulse, or effectively the difference between the frequency of the resonating spin system and the off-resonance RF pulse. $\omega_{B0}$ represents an additional frequency offset from resonance due to $B_0$ field inhomogeneity and/or chemical shift. $B_{1,peak}$ represents the maximum or substantially maximum value of $B_1(t)$ (i.e., the magnitude of the RF field at the highest or substantially highest point if the off-resonance RF pulse).

Figure 3:
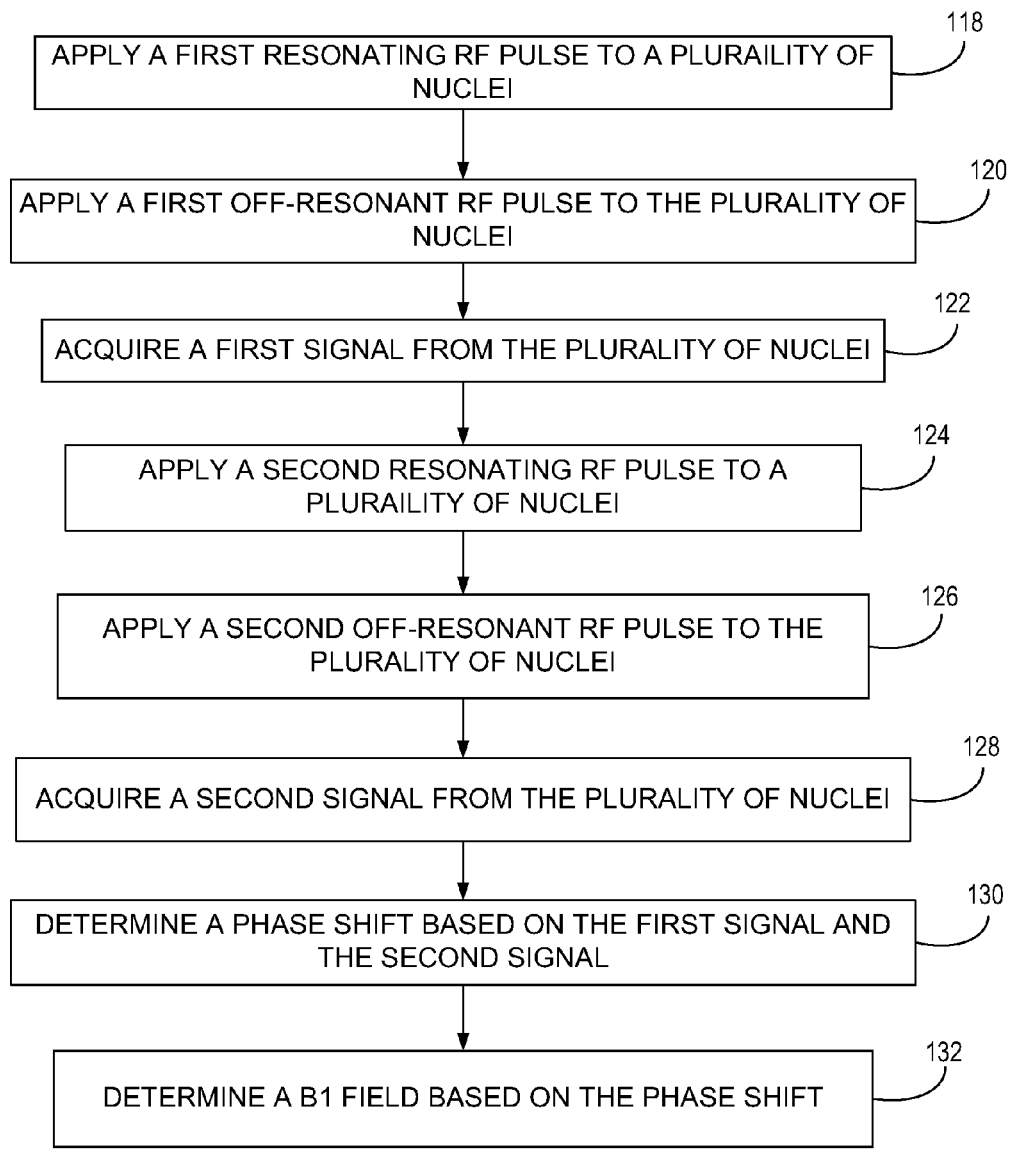
FIG. 3 is a flowchart depicting a technique for determining a $B_1$ field according to another embodiment of the invention.

Referring now to FIG. 3, a flowchart depicting a technique 116 for determining a $B_1$ field of a magnetic resonance coil or array according to another embodiment of the invention is shown. Technique 116 begins at block 118, where a first resonating RF pulse is applied to a plurality of nuclei. As discussed above with respect to FIG. 2, a resonating RF pulse is an RF pulse, which when applied to a plurality of nuclei excites the plurality of nuclei, causing them to precess at their resonant frequency. Though not shown in FIG. 3, it is contemplated that one or more RF pulses or pre-pulses may be played out prior to application of the first resonating RF pulse. After application of the first resonating RF pulse, a first off-resonance RF pulse is applied to the plurality of excited nuclei at block 120. In other words, the first off-resonance pulse is applied to the excited nuclei.

The application of the off-resonance pulse to the excited nuclei shifts the resonating frequency of the excited nuclei. As discussed above with respect to FIG. 2, an off-resonant RF pulse is an RF pulse that avoids or at least substantially avoids exciting the plurality of nuclei. As such, the frequency profile of an off-resonance RF pulse is chosen such that on-resonance excitation of the plurality of nuclei from such a pulse is avoided or at least substantially avoided.

Referring back to FIG. 3, in one embodiment, the first off-resonance RF pulse is a Fermi RF pulse at a first frequency other than the resonating frequency of the plurality of nuclei. It is noted, however, that rather than utilizing a Fermi pulse, other embodiments may utilize a resonating RF pulse different than a Fermi RF pulse. After application of the first off-resonance RF pulse, a first signal is acquired from the plurality of nuclei at block 122. It is contemplated that the first signal may be acquired as one or more spatial encoding gradients are played out, thus allowing for acquisition of 1D, 2D, or 3D image data.

After acquisition of the first signal, process control proceeds to block 124, where a second resonating RF pulse is applied to the plurality of nuclei. The application of the second resonating RF pulse causes the plurality of nuclei to re-excite. It is contemplated that one or more RF pulses or pre-pulses may precede the application of the second resonating RF pulse.

After application of the second resonating RF pulse, process control proceeds to block 126, where a second off-resonance RF pulse is applied to the plurality of excited nuclei. Like the first off-resonance RF pulse, the second off-resonance RF pulse has a frequency profile that avoids or at least substantially avoids resonating the plurality of nuclei, but rather shifts the resonating frequency of the plurality of nuclei. In the present embodiment, the second off-resonance RF pulse is at a second frequency that is different than the frequency of the first off-resonance RF pulse (i.e., the first frequency). A second signal is then acquired at block 128, after the application of the second off-resonance RF pulse.

It is contemplated that the application of the first resonating RF pulse, the application of the first off-resonance RF pulse, the acquisition of the first signal, the application of the second resonating RF pulse, the application of the second off-resonance RF pulse, and the acquisition of the second signal may occur during the same scan having any chosen repetition time (TR). It is also contemplated that such a scan may be an imaging scan. In such an instance, one or more spatial encoding gradients would be played out during acquisition of the first and second signals. As such, $B_1$ field information and imaging information is gathered during each acquisition (e.g., during acquisition of the first and second signals). The TR, the flip angles of the resonating RF pulses, and other parameters of an imaging sequence may be chosen to comport with any type of imaging sequence. For example, embodiments of the invention may incorporate spin echo, gradient echo, and echo planar-type imaging sequences. In addition, the parameters of the off-resonance RF pulse may be arbitrarily chosen as long as the RF pulse avoids or substantially avoids resonating the nuclei subjected to the magnetic fields.

It is also contemplated that each resonating RF pulse (i.e., the first and second resonating RF pulses) may be applied during a separate scan. For example, the application of the first resonating RF pulse, the first off-resonance RF pulse, and the acquisition of the first signal may occur during a first scan. In such an instance, the application of the second resonating RF pulse, the second off-resonance RF pulse, and the acquisition of the second signal may occur during a later or second scan. Additionally, spatial encoding gradients may be played out during the acquisition of the first and/or second signals.

Still referring to FIG. 3, after the second signal is acquired, process control proceeds to block 130, where a phase shift is determined based on the acquired first and second signals. According to one embodiment, a phase difference between the first and second signals is used to determine the phase shift.

According to such an embodiment, the phase difference between the first and second signals is determined by first converting the first and second signals to phase image data sets (i.e., a first phase image data set and a second phase image data set). The phase of each phase image data set corresponds to a combination of at least the transmit phase, $\phi_{Tx}$, the receive phase, $\phi_{Rx}$, the $B_0$ phase, $\phi_{B0}$, sequence phase $\phi_{Seq}$ and the Bloch-Siegert phase, $\phi_{BS}$. The phase difference between the two scans resulting from the Bloch-Siegert shift may be represented as follows:

$$\Delta\varphi_{BS} = \int_0^T \frac{\gamma B_1^2(t)}{2(\omega_{RF1}(t) + \omega_{B0})} - \int_0^T \frac{\gamma B_1^2(t)}{2(\omega_{RF2}(t) + \omega_{B0})}, \quad \text{(Eqn. 6)}$$

where $\Delta\phi_{BS}$ is the Bloch-Siegert phase difference between the two scans. $\phi_{RF}$ represents the offset frequency of the off-resonance RF pulse frequency. In other words, $\phi_{RF1}$ represents the frequency difference between the resonance frequency of the spin system, and the first off-resonance RF pulse. $\omega_{RF2}$ represents the frequency difference between the resonance frequency of the spin system, and the second off-resonance RF pulse. To continue, γ represents the gyromagnetic ratio and $B_1(t)$ represents the RF field of the off-resonance RF pulse, and $\omega_{B0}$ represents the frequency offset from resonance due to $B_0$ field inhomogeneity and/or chemical shift.

Further, if the first and second off-resonance RF pulses are configured to be applied on opposite sides of the spin resonance peak, in other words one off-resonance pulse at higher, and one at lower frequency than the spin resonance, $B_0$-inhomogeneity and chemical shift dependence of the Bloch-Siegert shift is greatly decreased. Here $\Delta\omega_{RF}$ is the average frequency offset of the two off-resonance pulse frequencies: $\Delta\omega_{RF}=(\Delta\omega_{RF1}-\Delta\omega_{RF2})/2$.

$$\Delta\varphi_{BS} \approx \int_0^T \frac{\gamma B_1^2(t)}{\Delta\omega_{RF}(t)}. \quad \text{(Eqn. 7)}$$

Similarly, the $\omega_{B0}$ dependent term of Eqn. 6 may also be avoided entirely if the offset of the first off-resonance frequency and the offset of the second off-resonance frequency are symmetric (e.g., $\omega_{RF1}=-\omega_{RF2}$, equivalently +/-$\omega_{RF}$ frequencies). That is, if the first off-resonance RF pulse is at a first frequency where the offset is +$\omega_{RF}$ and the second off-resonance RF pulse is a second frequency where the offset is -$\omega_{RF}$, transmit phases, receive phases, other sequence related phases, and phase shifts from off-resonance $B_0$ that are the same in both phase image data sets will be removed during subtraction. As such, a value of the Bloch-Siegert phase difference between the two signals, $\Delta\phi_{BS}$, that is dependent on the $B_1$ field and $\omega_{RF}$, but $B_0$ independent, is determined by Eqn. 7.

After determining the phase shift, process control proceeds to block 132, where a $B_1$ field is determined. The $B_1$ field determination is based on the previously determined Bloch-Siegert phase shift. In one embodiment, in cases where $\omega_{B0}$ can be disregarded, the $B_1$ field is represented in the following manner:

$$B_{1,peak} = \sqrt{\frac{\Delta\varphi_{BS}}{\int_0^T \frac{\gamma B_{1,normalized}^2(t)}{\omega_{RF}(t)}dt}}. \quad \text{(Eqn. 8)}$$

As one skilled in the art will appreciate, Eqn. 8 is effectively Eqn. 7 rewritten to solve for $B_1$. Accordingly, based on the first and second signals, $B_{1,peak}$ may be determined.

Figure 4:
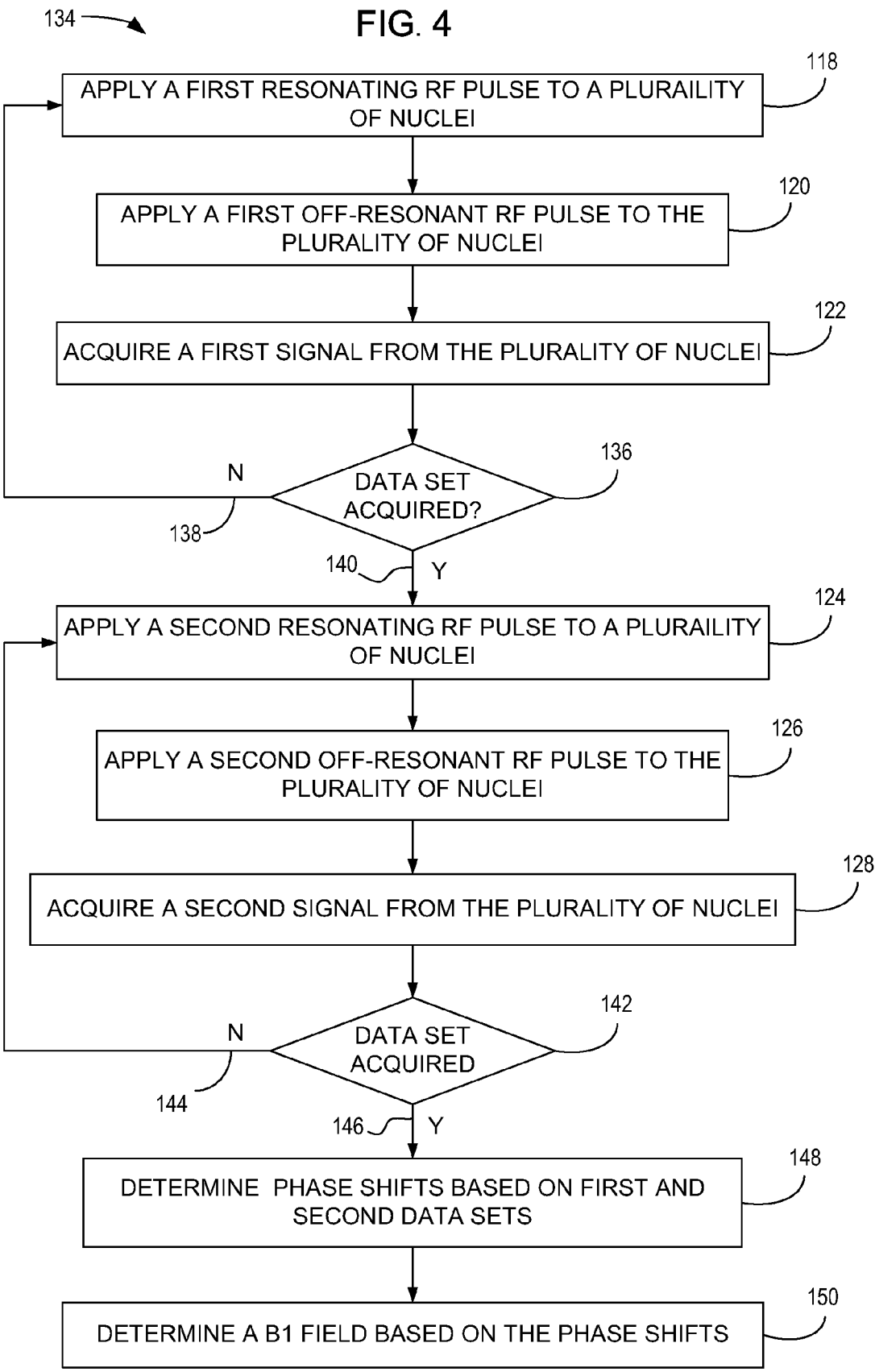
FIG. 4 is a flowchart depicting a technique for determining a $B_1$ field according to another embodiment of the invention.

Referring now to FIG. 4, a flowchart depicting a technique 134 for determining a $B_1$ field of a magnetic resonance coil or array according to another embodiment of the invention is shown. Technique 134 is similar to technique 116. However, after acquisition of the first signal at block 122, process control proceeds to decision block 136, where it is determined if a first data set is acquired. The first data set may include two or more lines of k-space or one or more lines of multiple k-spaces. It is also contemplated that first data set may include one or more image data sets. Whether or not the first data set includes k-space data or image data, the first data set includes information from more than one signal. If it is determined that the first data set is not acquired 138, process control proceeds to block 118, and the first resonating frequency is once again applied to re-excite the plurality of nuclei. It is contemplated that one or more RF pulses or pre-pulses may precede the application of the first resonating RF pulse. In addition, the parameters of the first resonating RF pulse may be different from the parameters of the previously applied first resonating RF pulse. Likewise, the parameters of the first off-resonance RF pulse may be different from the parameters of the previously applied off-resonance pulse.

If, on the other hand, it determined that the first data set is acquired 140, process control proceeds to block 124, where a second resonating RF pulse is applied to excite the plurality of nuclei. It is contemplated that one or more RF pulses or pre-pulses may precede the application of the second resonating RF pulse.

In a similar manner, after acquiring the second signal at block 128, process control proceeds to decision block 142, where it is determined if a second data set has been acquired. Similar to first data set, second data set may include more than one line of a single k-space or the second data set may include one or more lines of multiple k-spaces. Additionally, the second data set may include image data for one more image data sets. If it is determined that the second data set is not acquired 144, process control proceeds to block 124, where the second resonating RF pulse is applied to re-excite the plurality of nuclei. Again, it is contemplated that one or more RF pulses or pre-pulse may be applied prior to application of the second resonating RF pulse.

In addition, the parameters of the presently applied second resonating RF pulse may be different from the parameters of the previously applied second resonating RF pulse. Likewise, the parameters of the second off-resonant RF pulse may also change among applications.

If, on the other hand, it is determined that the second data set is acquired 146, process control proceeds to block 148, where phase shifts based on the first and second data sets are determined. Phase shifts may be determined in a manner similar to that as described above with respect to FIG. 3, utilizing Eqns. 6-8. However, rather than determining a single phase shift, multiple phase shifts are determined based on the multiple signals acquired. Process control then proceeds to block 150, and a $B_1$ field or field map is determined based on the phase shifts. According to one embodiment, the relationship of Eqn. 8 is used to determine the $B_1$ field map that embodies $B_1$ field inhomogeneities associated with the MR imaging coil(s).

Referring now to FIG. 5, a flowchart depicting a technique 152 for simultaneously determining a $B_1$ and $B_0$ field is shown according to an embodiment of the invention. Technique 152 begins at block 154, where a first scan utilizing an off-resonance RF pulse is implemented. In other words, a first scan, which may be an imaging scan, is implemented that utilizes at least one resonating RF pulse, at least one off-resonance RF pulse, and at least on signal acquisition that follows application of the off-resonance RF pulse. Process control then proceeds to block 156, where a second scan utilizing an off-resonating RF pulse is implemented. Similar to the first scan, the second scan includes at least one resonating RF pulse and at least one off-resonance pulse to shift the resonating frequency of the nuclei. The resonant frequency shift is followed by at least one signal acquisition.

After implementation of the second scan, process control proceeds to block 158, where a third scan that does not utilize an off-resonance RF pulse is implemented. The third scan utilizes at least one resonating RF pulse and at least one signal acquisition. However, the third scan does not utilize an off-resonance RF pulse to shift the resonating frequency of the plurality of nuclei subjected to the magnetic fields. It is contemplated that, in an alternate embodiment, the third scan is implemented prior to the first scan, between the first and second scans, or interleaved with the first and or second scans.

Referring back to the present embodiment, process control proceeds to block 160 after implementation of the third scan, and a $B_1$ field is determined based on the first and second scan. In one embodiment, the phase difference between the phase of the first scan, $\phi_1$, and the phase of the second scan, $\phi_2$, is used to determine the $B_1$ field. For example, as discussed above with respect to FIGS. 2-3, a phase gathered from a scan can be represented by at least the sum of the transmit phase, $\phi_{Tx}$, receive phase, $\phi_{Rx}$, $B_0$ phase, $\phi_{B0}$, sequence phase, $\phi_{Seq}$, and Bloch-Siegert phase. Where $\omega^{B0} \ll \omega_{RF}$, the Bloch-Siegert phase described by Eqn. 1 can be approximated by Taylor expansion by the following relationship:

$$\varphi_{BS} \approx \int_0^T \frac{\gamma B_1^2(t)}{2\omega_{RF}(t)} - \int_0^T \frac{\gamma B_1^2 \omega_{B0}}{2\omega_{RF}^2}. \quad \text{(Eqn. 9)}$$

This splits the Bloch Siegert phase shift into two terms: one $\omega_{B0}$-dependent and one $\omega_{B0}$-independent.

$$\varphi_{BS} = \varphi\left(\frac{\gamma B_1^2}{2\Delta\omega_{RF}}\right) - \varphi\left(\frac{\gamma B_1^2 \Delta\omega_{B0}}{2\Delta\omega_{RF}^2}\right), \quad \text{(Eqn. 10),}$$

where:

$$\varphi\left(\frac{\gamma B_1^2}{2\Delta\omega_{RF}}\right) = \int_0^T \frac{\gamma B_1^2(t)}{2\omega_{RF}(t)}, \quad \text{(Eqn. 11)}$$

$$\varphi\left(\frac{\gamma B_1^2 \Delta\omega_{B0}}{2\Delta\omega_{RF}^2}\right) = \int_0^T \frac{\gamma B_1^2 \Delta\omega_{B0}}{2\Delta\omega_{RF}^2}.$$

Accordingly, the phase of the first scan can be represented as follows:

$$\phi_1 = (\phi_{Tx} + \phi_{Rx} + \phi_{B0} + \phi_{Seq}) + \varphi\left(\frac{\gamma B_1^2}{2\Delta\omega_{RF}}\right) - \varphi\left(\frac{\gamma B_1^2 \Delta\omega_{B0}}{2\Delta\omega_{RF}^2}\right). \quad \text{(Eqn. 12)}$$

Next, if $-\Delta\omega_{RF}$ is implemented in the second scan, the phase of the second scan can be represented as follows:

$$\phi_2 = (\phi_{Tx} + \phi_{Rx} + \phi_{B0} + \phi_{Seq}) - \varphi\left(\frac{\gamma B_1^2}{2\Delta\omega_{RF}}\right) - \varphi\left(\frac{\gamma B_1^2 \Delta\omega_{B0}}{2\Delta\omega_{RF}^2}\right). \quad \text{(Eqn. 13)}$$

If RF excitation is applied at frequencies symmetrically around the water resonance peak, the $B_1$ field can be determined in a $B_0$ independent manner from the phase difference between the first scan and the second scan. That is, $\phi_1 - \phi_2 \Rightarrow B_1$.

After determining the $B_1$ field, process control proceeds to block 162, where a $B_0$ field based on the first, second, and third scans is determined. Since the third scan was implemented without using an off-resonance RF pulse to shift the resonating frequency of the nuclei subjected to the imaging, the phase of the third scan can be represented in the following manner:

$$\phi_3 = (\phi_{Tx} + \phi_{Rx} + \phi_{B0} + \phi_{Seq}) \quad \text{(Eqn. 14).}$$

Accordingly, the $B_0$ field may be determined from the phase difference between the third scan and the first and second scans (i.e., $2\phi_3 - (\phi_1 + \phi_2) \Rightarrow B_0$).

For nonsymmetric RF frequency offsets (i.e., $\Delta\omega_{RF1} \neq \Delta\omega_{RF2}$), B1 and B0 can still be determined by solving the system of equations defined by Eqn. 10, where $\Delta\omega_{RF} = \Delta\omega_{RF1}$, Eqn. 11 where $\Delta\omega_{RF} = \Delta\omega_{RF2}$, and Eqn. 12.

A technical contribution for the disclosed method and apparatus is that it provides for processor implemented $B_1$ field determination.

In accordance with one embodiment, a magnetic resonance imaging (MRI) apparatus includes a magnetic resonance imaging (MRI) system having a plurality of gradient coils positioned about a bore of a magnet, and an RF transceiver system and an RF switch controlled by a pulse module to transmit RF signals to an RF coil assembly to acquire MR images, and a computer. The computer is programmed to apply a first off-resonant radio frequency (RF) pulse at a first frequency different than the resonant frequency to a plurality of nuclei excited at a resonant frequency, acquire a first signal from the plurality of nuclei after application of the first off-resonant RF pulse, determine a phase shift from the first signal based on the first off-resonant RF pulse, determine a B1 field based on the phase shift, and store the B1 field on a computer readable storage medium.

In accordance with another embodiment, a computer readable storage medium includes a computer program stored thereon. The computer program includes instructions which when executed by a computer cause the computer to cause a pulse generator to apply a first off-resonant radio frequency (RF) pulse to a plurality of excited nuclei, receive a first signal from the plurality of excited nuclei via at least one magnetic resonant (MR) receive coil after application of the first off-resonant RF pulse, determine a phase shift induced by the first off-resonant RF pulse, determine a B1 field based on the phase shift, and store the B1 field on a storage device coupled to an MR imaging apparatus. The first off-resonant RF pulse is configured to shift a resonant frequency of the plurality of nuclei.

In accordance with yet another embodiment, a method of determining a magnetic field includes shifting a resonating frequency of a plurality of nuclei after the plurality of nuclei are excited at a first resonating frequency, acquiring a first signal with a magnetic resonance (MR) receive coil from the plurality of nuclei after shifting the resonating frequency, determining a phase shift based on the first signal, and storing the phase shift on a computer readable storage medium coupled to an MR apparatus.

The present invention has been described in terms of the preferred embodiment, and it is recognized that equivalents, alternatives, and modifications, aside from those expressly stated, are possible and within the scope of the appending claims.

What is claimed is:

1. A magnetic resonance imaging (MRI) apparatus comprising:
   a magnetic resonance imaging (MRI) system having a plurality of gradient coils positioned about a bore of a magnet, and an RF transceiver system and an RF switch controlled by a pulse module to transmit RF signals to an RF coil assembly to acquire MR images; and
   a computer programmed to:
      apply a first off-resonant radio frequency (RF) pulse at a first frequency to a plurality of nuclei excited at a resonant frequency, wherein the first frequency is different than the resonant frequency;
      acquire a first signal from the plurality of nuclei after application of the first off-resonant RF pulse;
      determine a phase shift from the first signal, wherein the phase shift is based on the first off-resonant RF pulse;
      determine a B1 field based on the phase shift relative to a reference scan; and
      store the B1 field on a computer readable storage medium.

2. The MRI apparatus of claim 1 wherein the computer is further programmed to:
   apply a first resonant RF pulse to the plurality of nuclei before application of the first off-resonant RF pulse to excite the plurality of nuclei at the resonant frequency;
   apply a second resonant RF pulse to the plurality of nuclei to excite the plurality of nuclei at the resonant frequency;
   apply a second off-resonant RF pulse to the plurality of nuclei after application of the second resonant RF pulse, wherein the second off-resonant RF pulse is at a second frequency different than the resonant frequency and the first frequency;
   acquire a second signal from the plurality of nuclei after application of the second off-resonant RF pulse; and
   wherein the computer, in being programmed to determine the phase shift, is programmed to determine a first phase difference between the first signal and the second signal to determine the phase shift, wherein the phase shift is further based on the second off-resonant RF pulse.

3. The MRI apparatus of claim 2 wherein the computer is further programmed to:
   repeat application of the first resonant RF pulse and the first off-resonant RF pulse and repeat acquisition of the first signal until a first image data set is acquired;
   repeat application of the second resonant RF pulse and the second off-resonant RF pulse and repeat acquisition of the second signal until a second image data set is acquired; and
   determine a plurality of spatially dependent phase differences between the first and second image data sets, wherein the plurality of spatially dependent phase differences comprises the first phase difference.

4. The MRI apparatus of claim 2 wherein the computer is further programmed to:
   apply a spatial encoding gradient to the plurality of nuclei during acquisition of the first signal; and
   apply the spatial encoding gradient to the plurality of nuclei during acquisition of the second signal.

5. The MRI apparatus of claim 2 wherein the first off-resonant RF pulse is a Fermi pulse and the second off-resonant RF pulse is a Fermi pulse.

6. The MRI apparatus of claim 2 wherein the first frequency and the second frequency are substantially symmetric about a water resonance frequency.

7. The MRI apparatus of claim 2 wherein the computer is further programmed to:
   determine a first B1 magnetic field map based on the first phase difference; and
   display the first B1 magnetic field map to a user.

8. The MRI apparatus of claim 7 wherein the computer is further programmed to:
   apply a third resonant RF pulse at the resonant frequency to the plurality of nuclei;
   acquire a third signal from the plurality of nuclei after application of the third resonant RF pulse;
   determine if a frequency center point of the first off-resonant RF pulse and a frequency center point of the second off-resonant RF pulse are asymmetric about a water resonance frequency based on the first, second, and third signals; and
   determine a B0 field based on the determination.

9. The MRI apparatus of claim 2 wherein the application of the first resonant RF pulse and the first off-resonant RF pulse occurs during a first scan, and wherein the second resonant RF pulse and the second off-resonant RF pulse occurs during a second scan.

10. The MRI apparatus of claim 9 wherein the first and second scans are imaging scans.

11. The MRI apparatus of claim 2 wherein the first resonant RF pulse, the first off-resonant RF pulse, the second resonant RF pulse, and the second off-resonant RF pulse occur during a first scan.

12. The MRI apparatus of claim 11 wherein the first scan is an imaging scan.

13. A non-transitory computer readable storage medium having stored thereon a computer program comprising instructions which when executed by a computer cause the computer to:
   cause a pulse generator to apply a first off-resonant radio frequency (RF) pulse to a plurality of excited nuclei, the first off-resonant RF pulse configured to shift a resonant frequency of the plurality of nuclei;

receive a first signal from the plurality of excited nuclei via at least one magnetic resonant (MR) receive coil after application of the first off-resonant RF pulse;

determine a phase shift induced by the first off-resonant RF pulse;

determine a B1 field based on the phase shift; and store the B1 field on a storage device coupled to an MR imaging apparatus.

14. The computer readable storage medium of claim 13 having further instructions to cause the computer to:

apply a first resonant RF pulse to the plurality of nuclei to excite the plurality of nuclei, the first resonant RF pulse at a first frequency substantially equivalent to a resonant frequency of the plurality of nuclei;

apply a second resonant RF pulse to the plurality of nuclei after acquisition of the first signal to excite the plurality of nuclei;

apply a second off-resonant RF pulse to the plurality of excited nuclei after application of the second resonant RF pulse, the second off-resonant RF pulse configured to shift the resonant frequency of the plurality of nuclei;

receive a second signal from the plurality of excited nuclei after application of the second off-resonant RF pulse; and determine a phase difference between the first signal and the second signal; and wherein the instructions that cause the computer to determine the phase shift cause the computer to determine the phase shift based on the phase difference.

15. The computer readable storage medium of claim 14 having further instructions to cause the computer to generate a B1 map based on the phase shift.

16. The computer readable storage medium of claim 14 having further instructions to cause the computer to determine a transmit gain based on the phase shift.

17. A method of determining a magnetic field comprising:

shifting a resonating frequency of a plurality of nuclei after the plurality of nuclei are excited at a first resonating frequency;

acquiring a first signal with a magnetic resonance (MR) receive coil from the plurality of nuclei after shifting the resonating frequency; and determining a phase shift based on the first signal;

storing the phase shift on a computer readable storage medium coupled to an MR apparatus; and determining a B1 field based on the phase shift.

18. The method of claim 17 wherein shifting the resonating frequency of the plurality of nuclei comprises applying a first off-resonance RF pulse to the plurality of nuclei excited at the first resonating frequency.

19. The method of claim 18 further comprising:

applying a first resonating RF pulse to the plurality of nuclei before applying the first off-resonance RF pulse to excite the plurality of nuclei at the first resonating frequency;

applying a second resonating RF pulse to the plurality of nuclei after acquiring the second signal to excite the plurality of nuclei at the first resonating frequency;

shifting the resonating frequency of the plurality of nuclei excited at the first resonating frequency via application of a second off-resonance RF pulse after applying the second resonating RF pulse;

acquiring a second signal from the plurality of nuclei after application of the second off-resonance RF pulse; and determining a phase difference between the first and second signals; and wherein determining the phase shift comprises determining the phase shift based on the phase difference.

20. The method of claim 19 further comprising generating a magnetic field map based on the phase difference between the first and second signals.

* * * * *